United States Patent [19]

Schmidt et al.

[11] Patent Number: 4,525,266
[45] Date of Patent: Jun. 25, 1985

[54] ELECTROCHEMICAL GAS SENSOR

[75] Inventors: John C. Schmidt, Baltimore; Donald N. Campbell, Timonium; Sandra B. Clay, Baltimore, all of Md.

[73] Assignee: Allied Corporation, Morristown, N.J.

[21] Appl. No.: 541,630

[22] Filed: Oct. 13, 1983

[51] Int. Cl.³ .............................................. G01N 27/46
[52] U.S. Cl. .................... 204/412; 204/415; 204/431; 204/432
[58] Field of Search ............... 204/412, 415, 1 F, 431, 204/432

[56] References Cited

U.S. PATENT DOCUMENTS

| | | | |
|---|---|---|---|
| 3,223,597 | 12/1965 | Hersch | 204/431 X |
| 3,223,608 | 12/1965 | Hersch | 204/431 |
| 3,403,081 | 9/1968 | Rohrback et al. | 204/412 X |
| 3,436,320 | 4/1969 | Marsh | 204/412 X |
| 3,523,872 | 8/1970 | Hersch et al. | 204/1 F |
| 3,806,428 | 4/1974 | Beltzer | 204/431 X |
| 3,824,166 | 7/1974 | Deibert | 204/412 X |
| 3,980,530 | 9/1976 | Hueser | 204/1 F |
| 4,028,197 | 6/1977 | Capuano | 204/1 B |
| 4,029,563 | 6/1977 | Binder et al. | 204/1 F X |
| 4,127,462 | 11/1978 | Blurton et al. | 204/412 |
| 4,154,660 | 5/1979 | Micko | 204/412 X |
| 4,166,775 | 9/1979 | Bruckenstein et al. | 204/412 X |
| 4,169,779 | 10/1979 | Tataria et al. | 204/1 T X |
| 4,184,937 | 1/1980 | Tataria et al. | 204/412 |
| 4,201,634 | 5/1980 | Stetter | 204/412 X |
| 4,265,714 | 5/1981 | Nolan et al. | 204/1 B |
| 4,285,796 | 8/1981 | Stoner et al. | 204/412 X |
| 4,302,315 | 11/1981 | Stetter et al. | 204/412 |
| 4,326,927 | 4/1982 | Stetter et al. | 204/412 X |
| 4,409,069 | 10/1983 | Luft | 204/412 X |

Primary Examiner—G. L. Kaplan
Assistant Examiner—Nam X. Nguyen
Attorney, Agent, or Firm—Robert M. Trepp; Bruce L. Lamb

[57] ABSTRACT

An electrochemical gas detection cell, particularly suitable for detecting $H_2S$, includes an electrochemical gas sensor which has a reference electrode, a sensing electrode and a counter electrode. The counter electrode is composed of carbon. The sensing electrode is composed of either gold or platinum and the reference electrode is composed of platinum. Circuitry is provided to supply voltage to the electrodes, the sensing electrode bias can be held below 300 mv., with respect to the reference electrode. The agent $H_2S$ can be readily detected when the bias is about 250 mv. The cell is associated with signal processing circuitry which produce audible and visual outputs. A nonaqueous electrolyte is provided. The electrolyte may be composed of either propylene carbonate or n-methyl-2-pyrrolidone and one of conductive compatible salts, such as tetrabutyl ammonium tetrafluoroborate.

15 Claims, 4 Drawing Figures

ELECTROCHEMICAL GAS SENSOR

BACKGROUND OF THE INVENTION

The invention relates to an electrochemical gas sensor, an electrochemical gas detection cell, a system for detecting gas using such a cell and a filter which may be used in the cell. More particularly, the present invention is concerned with an electrochemical hydrogen sulfide sensor, an electrochemical hydrogen sulfide detection cell, a system using the cell and a filter which may be used in the cell. The invention is also concerned with a system for detecting gas which is constructed from modular parts.

Examples of prior art electrochemical sensors used in detection cells, which sensors include a sensing electrode, a reference electrode and a counter electrode are illustrated in respective U.S. Pat. Nos. 3,776,832 and 3,925,183 to Oswin et al. entitled respectively "Electrochemical Detection Cell" and "Gas Detecting and Quantitative Measuring Device" and issued respectively Dec. 4, 1983 and Dec. 9, 1975. The electrodes are of conventional types which are expensive and must be operated at conventional, relatively high voltage levels.

The U.S. Pat. No. 3,776,832 to Oswin et al., supra, describes a three-electrode electrochemical gas sensor which can be adapted to measure oxidizable or reducible gases such as $H_2S$, $CO$, $Cl_2$ and hydrazine, as well as other gases. This particular known cell has two shortcomings. Firstly, it requires an aqueous electrolyte which has a limited shelf life due to evaporation of the electrolyte. Secondly, the temperature range within which the cell can operate is limited due to the possibility of freezing of the electrolyte.

The shortcomings noted above as a result of using an aqueous electrolyte have been recognized for some time. It has been proposed and disclosed in U.S. Pat. No. 4,169,779 to Tataria et al. entitled "Electrochemical Cell for the Detection of Hydrogen Sulfide" and issued on Oct. 2, 1979 to replace the aqueous electrolyte in a three-electrode cell with a nonaqueous electrolyte, which has a considerably lower freezing point and vapor pressure than aqueous electrolyte. The three-electrode sensor of this known electrochemical cell includes a counter electrode of gold or platinum black, relatively expensive materials. Moreover, the sensing electrode bias, with respect to that of the platinum air reference electrode is maintained in the range of from 300 mv. to 1100 mv., preferably in the range of from 500 mv. to 1000 mv. with the result that oxidizable interferents which may be present in many test environments cause erroneous responses, that is, result in decreased specificity.

Additional examples of electrochemical detection cells are disclosed and illustrated in the U.S. patents identified as follows:

| U.S. Pat. No. 4,040,805 | Nelms et al. | August 9, 1977 |
| U.S. Pat. No. 4,048,041 | David et al. | September 13, 1977 |
| U.S. Pat. No. 4,127,461 | Paulen | November 28, 1978 |
| U.S. Pat. No. 4,184,937 | Tataria et al. | January 22, 1980 |
| U.S. Pat. No. 4,201,634 | Setter | May 6, 1980 |
| U.S. Pat. No. 4,227,984 | Dempsey et al. | October 14, 1980 |
| U.S. Pat. No. 4,235,097 | Kring et al. | November 25, 1980 |
| U.S. Pat. No. 4,271,121 | Diller et al. | June 2, 1981. |

Of particular interest as background prior art is the publication J. A. Plambeck, *Electroanalytical Chemistry*, Wiley-Interscience, pages 50–51, New York, N.Y. (1963) which is concerned with circuitry, generally referred to as a potentiostat, for maintaining a sensing electrode of an electrochemical cell at a fixed potential with respect to its reference electrode.

SUMMARY OF THE INVENTION

An object of the present invention is to provide a stable, relatively inexpensive electrochemical gas sensor which includes a sensing electrode, a reference electrode and a counter electrode.

An additional object of the present invention is to provide an electrochemical gas sensor which includes a sensing electrode, a reference electrode and a counter electrode, the counter electrode being made of inexpensive material.

Another object of the present invention is to provide an electrochemical gas sensor which includes a sensing electrode, a reference electrode and a counter electrode which in specific, has good selectivity and may be operated at low voltage level.

A further object of the present invention is to provide an electrochemical gas detection cell which includes an electrochemical sensor having a sensing electrode, a reference electrode and a counter electrode, made of inexpensive material, in operative association with a gas filter and members arranged to supply an electrolyte.

A still additional object of the present invention is to provide a gas filter which is useful in the gas detection cell of the invention.

A still further object of the present invention is to provide a system for detecting gas which includes a gas sensor constructed in accordance therewith.

A still additional object of the present invention is to provide a system for detecting gas which is modular in nature and may be used as a portion thereof in a gas sensor in accordance therewith.

It is yet a further object of the present invention to provide a nonaqueous electrolyte which may be used in a gas sensor.

In accordance with the gas sensor aspect of the invention, a sensor having a sensing electrode, a reference electrode and counter electrode is provided, the counter electrode being made of carbon instead of gold or platinum. The sensor is particularly suitable for detecting hydrogen sulfide.

The invention can also be viewed as gas detection cell which includes, in addition to a sensor having a counter electrode of carbon, a sensing electrode and a reference electrode, a filter, provisions for supplying an electrolyte and conductive connections to the electrodes.

The invention can also be seen as constituted by a filter in a gas detection cell and as a filter particularly suitable for use in a gas detection cell. The filter is constituted by a laminate of at least one dimethyl silicone membrane and at least one spacer made of chemically inert material which is rigid, one such material is sold under the trademark Tefzel ® of the Dupont Company of Wilmington, Del., and at least one membrane of polypropylene (PPE), a suitable commerically available 1 mm. thick membrane being available. The filter is particularly useful in association with an electrochemical hydrogen sulfide detection sensor.

In its filter aspect, the invention can also be reviewed as a filter in a gas detection cell and as a filter constituted by a laminate as noted above with firebrick treated with a material, for example ethanolamine, which can remove interferents.

In yet another aspect, the invention is a system for detecting gas which includes a potentiostat and a gas detection cell constituted by a sensor having a counter electrode of carbon, a sensing electrode and a reference electrode, provisions for supplying an electrolyte and a filter. The system is especially suitable for detecting hydrogen sulfide.

In its modular aspect, the invention can be viewed as including a case having an opening therein for communication with an ambient and within which a circuit package, preferably potted, is positioned. The gas detection cell is removably, slideably fitted into the case, the sensor and some associated parts thereof being removeably associated with a portion of a housing, which may include a chamber which stores an electrolyte. A filter is provided between the opening in the case and the sensor, which filter can be removed from the case with the sensor and disassociated therefrom. The housing may be provided with a battery-holding compartment or compartments.

BRIEF DESCRIPTION OF THE DRAWINGS

FIG. 1 is a pictorial view of the case, within which a gas sensor with its associated members constituting an electrochemical gas sensing cell, and circuitry may be placed, the case being associated with an alligator clip allowing a user to attach the case to an article of clothing or the like.

DETAILED DESCRIPTION OF THE PREFERRED EMBODIMENTS

Figure 1:
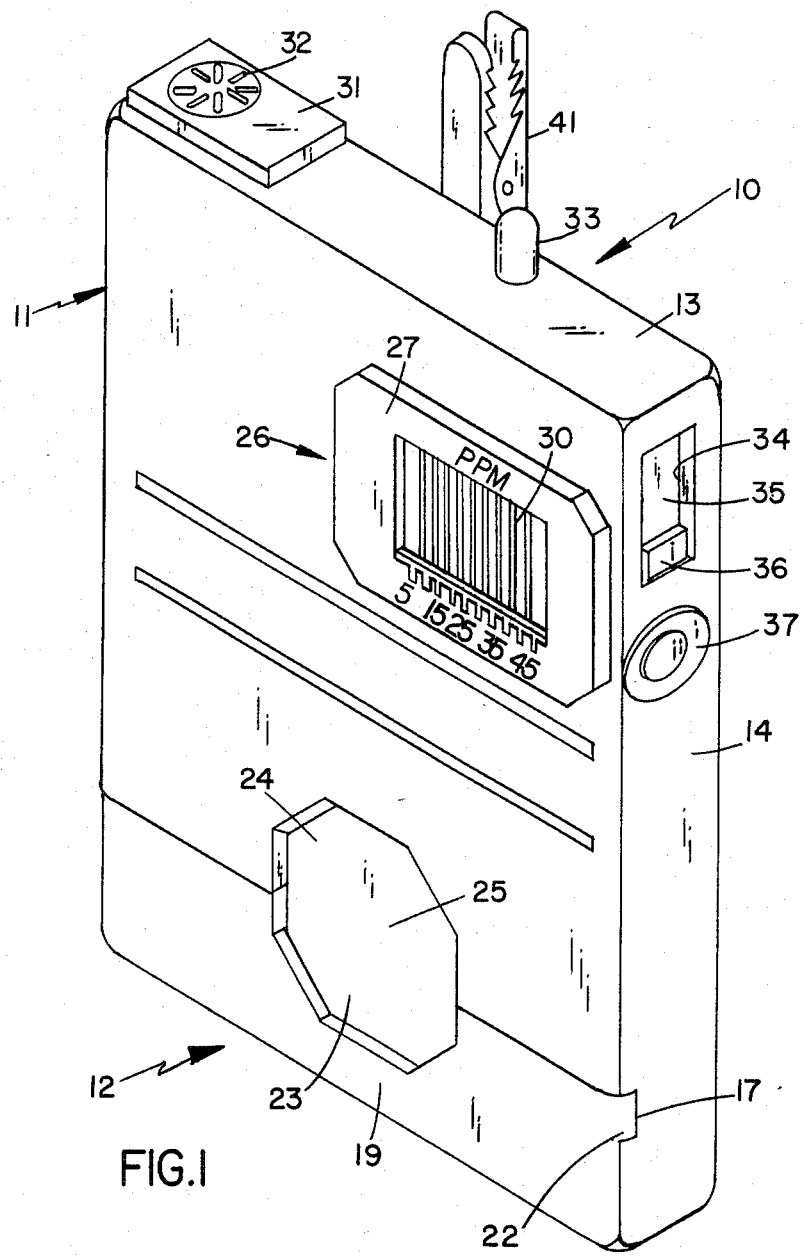
Figure 2:
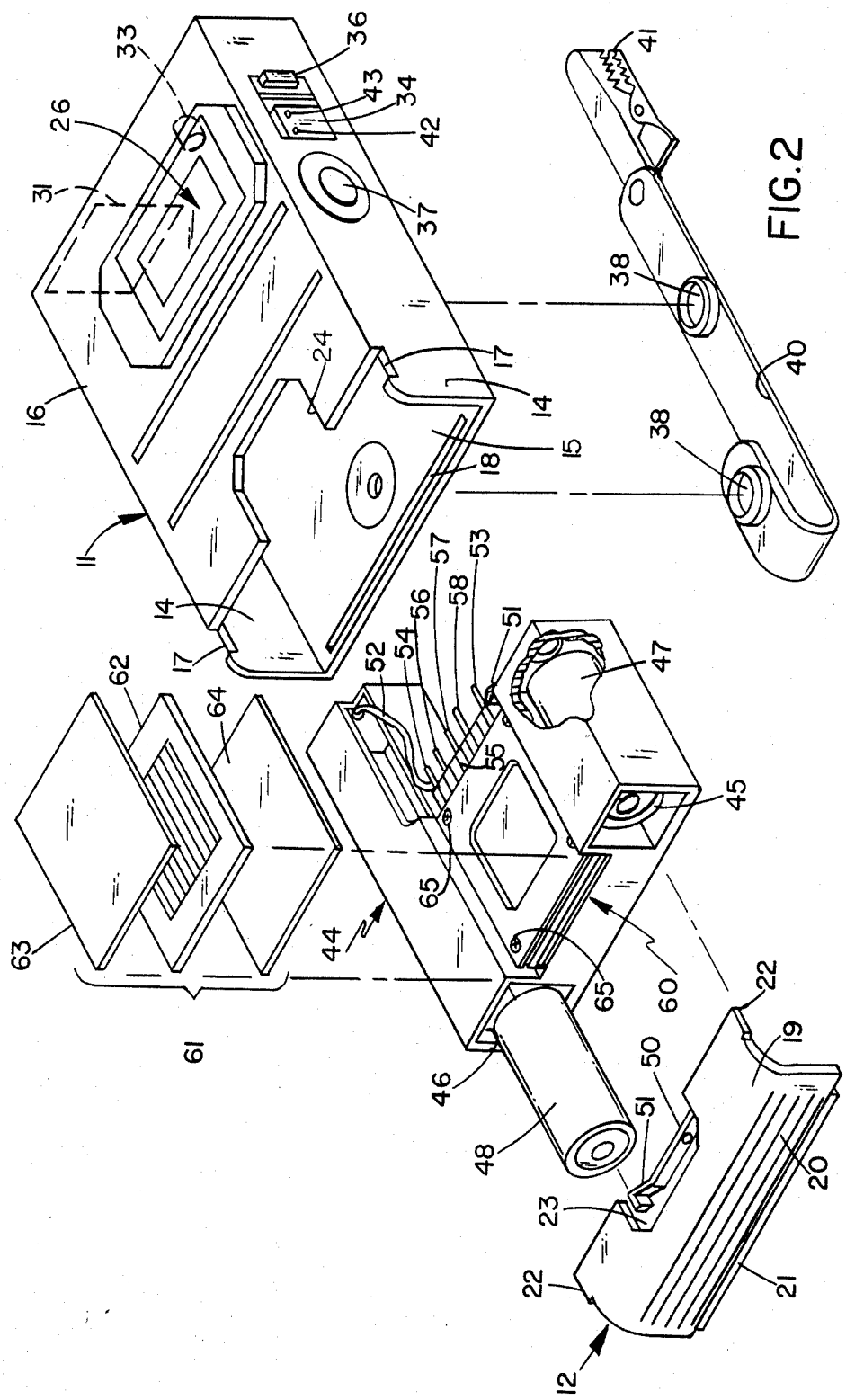
FIG. 2 is an exploded, pictorial view of the case shown in FIG. 1 with relative positions of some of the components housed therein being illustrated.

Referring to FIGS. 1 and 2, a suitable case within which to position an electrochemical gas sensor with its associated components and circuitry is generally designated by the numeral 10. The case 10 is constituted by two members, an upper member 11 and a lower member 12, both made of a suitable molded plastics material. The upper member 11 is constituted by a single piece which includes an upper end wall 13, a pair of spaced-apart side walls 14 which extend downwardly from the upper end wall 13, and a back wall 15 which extends between the side walls 14 and is of corresponding length. Spaced from the back wall 15 is a front wall 16 which extends between the side walls 14 from the upper end wall 13 and has a length corresponding approximately to 0.8 of the length of the side walls 14, leaving a frontal opening. The upper member 11 is open at its lower end. The side walls 14 each have a respective notch 17 formed therein at their respective junctures with the lower end of the front wall 16. The back wall 15 is provided adjacent its lower end a slot 18 (FIG. 2) which extends between the vicinities of the intersection of the back wall 15 with the respective side walls 14, but falls slightly short thereof.

The second member 12 constituting the case 10, has a front wall 19 and a bottom end wall 20. The bottom end wall 20 is provided with an elongated detent 21 which is positioned so that it may be fitted into the groove 18 in the back wall 15 of the member 11. The front wall 19 of the member 12 is provided with a pair of detents 22 which extend downwardly and are positioned so that they can be fitted respectively into the pair of respective notches 17 in the side walls 14 of the member 11. The front wall 16 and the front wall 19 of the respective members 11 and 12 are respectively provided with cutouts 23 and 24 which are so positioned that when the lower member 12 is snap-fitted to the upper member 11, the cut-outs 23, 24 become aligned and define an aperture 25 (FIG. 1) in the box-like case 10. The aperture 25 is of such a size that a filter, which is to reject interferents while passing the gaseous agent to be detected, may be positioned when the electrochemical gas sensor is in operation. The front wall 16 of the upper member 11 is provided in the vicinity of its upper right-hand portion with an aperture within which a bar graph indicator, which may be a liquid crystal display, generally designated by the numeral 26 can be viewed. The indicator 26, which is surrounded by a frame member 27 which may be made of a plastics material, extends about the visual part of the indicator 26 and is provided with a paper overlay which has markings thereon constituting a scale, illustrated as extending from 0 to 50 and has printed thereon, as illustrated, the letters PPM, which refers to parts-per-million. As illustrated, the indicator 26 has a number of its lines 30, extending from top to bottom of the indicator, and which as illuminated indicate the presence of about 40 parts-per-million of a gaseous agent, $H_2S$ in the particularized invention.

The upper wall 13 is provided with a rectangular aperture in its left-most portion through which a buzzer 31 extends, apertures 32 through which sound may be transmitted being provided so as to provide an audible indication of the presence of a gaseous agent, in particular, $H_2S$, over a set given level. The top wall 13 is provided with a second circular aperture through which a light-passing plastic member 33 extends so that light, for example, red light from a light emitting diode (LED), can be passed providing a visual indication of the presence at and above a given threshhold level of the gaseous agent, in particular, $H_2S$, sought to be detected.

The right side wall 14 of the upper member 11 includes a rectangular aperture 34 beneath which a slidable member 35, which can be made of the same plastics material as the members 11 and 12 and which is provided with an upstanding bar portion 36 thereon, is positioned and can be moved by a user, using his finger to apply force to the bar portion 36, from a closed position (FIG. 1) to an open position (FIG. 2). The right sidewall 14 is also provided with a circular aperture through which a button member 37 extends; a user can press inwardly on the button member 37 to turn the indicator ON and effect a readout of the sensor.

The outside of the backwall 15 of the member 11 is provided with a pair of male snaps (not visible) positioned to receive female snaps 38 which are positioned on an elongated strap 40 which carries on its distal end an alligator clip 41 or the like. The snaps 38, when positioned on the corresponding male snaps, on the back of the wall 15, allow a user using the alligator clip 41 to removably fix the case 10 conveniently on an article of clothing, belt or the like. The alligator clip 41 of course, could be suitably replaced with another clamping or clasping member which could serve a similar purpose.

Figure 4:
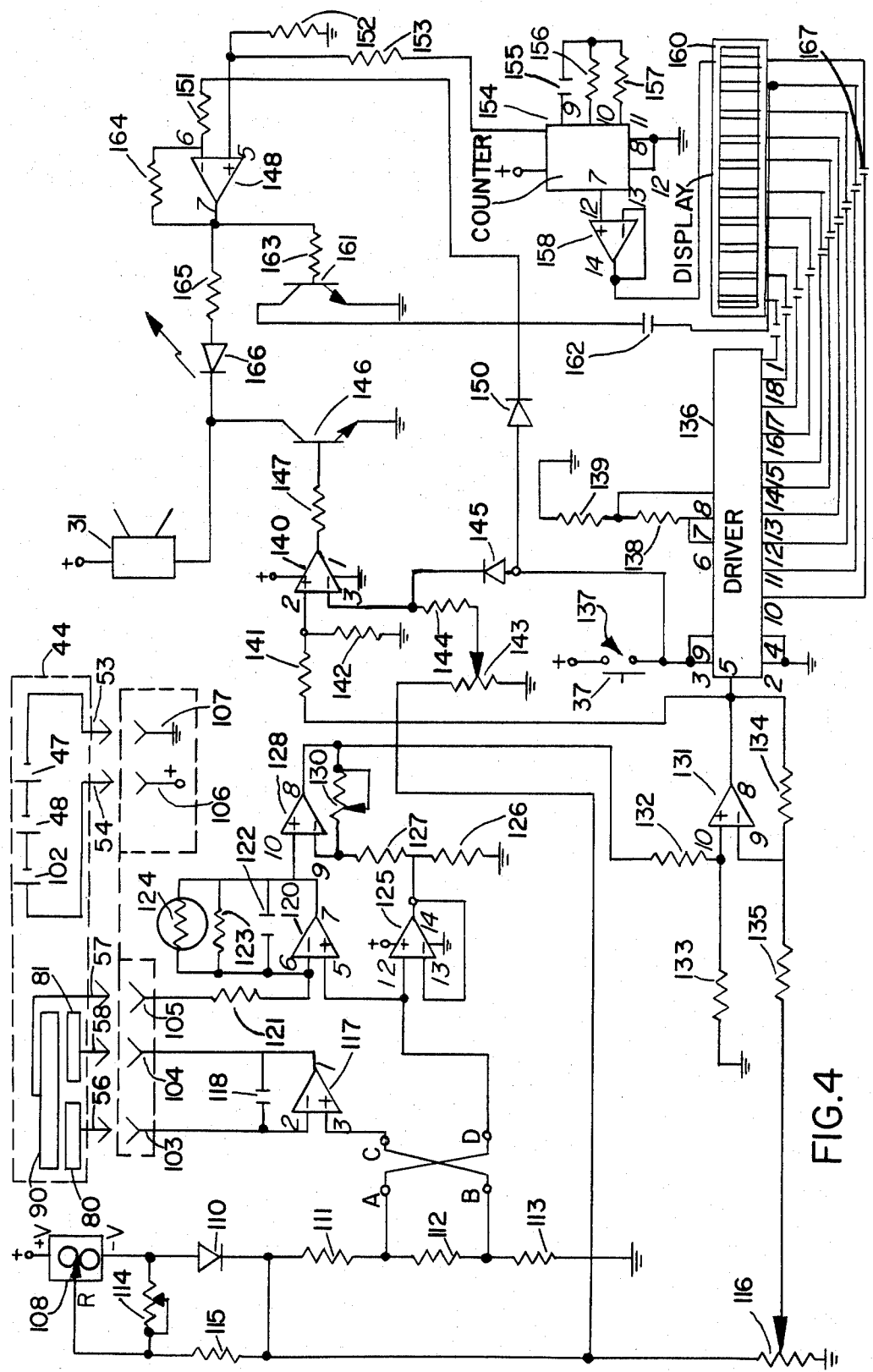
FIG. 4 is a schematic diagram of a circuit which may be connected to the electrodes of the gas detection cell illustrated in FIG. 3 so as to function as a potentiostat and as signal processing circuitry which provides visual and audible output signals as a function of the presence of a gaseous agent to be detected, the electrodes being shown diagrammatically.

As seen in FIG. 2, the window-like aperture 34, when the slidable member 35 has been placed in its open position exposes the heads of a set screw 42 and a set screw 43 which are associated respectively with respective circuit components and provide respectively for zero adjustment and span adjustment of the liquid crystal indicator 26, features which are to be discussed in more detail in conjunction with FIG. 4.

As visible in FIG. 2, a housing generally designated by the numeral 44 and made as an integral single piece of plastics material, is shaped and dimensioned so that it may be removably fitted into the case 10 against friction forces between some of its outwardly facing surfaces and corresponding inwardly facing surfaces of the case 10 by gentle pressure of a user's fingers for example. The housing 44 includes a chamber 45, shown towards the right in FIG. 2, and a chamber 46, shown to the left in FIG. 2 and of approximately twice the length of the chamber 45. A portion of battery 47 is visible in the chamber 45 through a broken away portion thereof and a second battery 48, is shown outside the chamber 46. A further battery is provided within the chamber 46 and, when the members shown in FIG. 2 are assembled for operation, the battery 48 would be positioned within the chamber 46 in contact with the second battery therein. A resilient conductive bar 50, having an upwardly extending portion 51 on each of its ends, only one being visible in FIG. 2, is fixed to the wall 20 of the member 12, to provide an electrical connection between the battery 48 and the battery 45 which, with the third battery, supply voltage to the circuitry which is positioned within the upper member 11 and preferably is potted therein. The electrical connections to the circuitry from a series connection of the batteries 47, 48 and the third battery within the chamber 46 is provided by a pair of respective leads 51 and 52, via respective pins 53 and 54 to which the respective leads 51, 52 are attached. The pins 53 and 54 are carried by a header 55 which also carries pins 56–58, which provide electrical contact between circuit components and the three electrodes of a gas detection cell generally designated by the numeral 60. The housing 44 also include a hollow cavity from beneath the gas detection cell 60 which is used as a reservoir for an electrolyte.

The gas detection cell 60 includes a laminated filter 61 which allows passage of the gaseous agent, in particular $H_2S$, to be detected while substantially filtering out interferents. As illustrated, the filter 61 includes a support, shown in form of a grill 62 on opposite sides of which are respectively positioned a first membrane 63 and a second membrane 64. In a preferred embodiment an inert material, firebrick for example, which is a carrier for a material which can remove interferents, is positioned within the grill 62 between the membranes 61 and 63. The details of construction and nature of the filter 61 are to be discussed in more detail below in conjunction with FIG. 3. When assembled, the filter 61 is a single component which can be placed over those portions of the gas detection cell 60 which are held together by four screws 65 (FIGS. 2,3) which extend into bores in the housing 44, threaded metal inserts may be fixed in the bores for receiving the screws. The filter 61 thus can be readily removed and replaced without removing all of the components of the gas detection cell 60, or even those members constituting its electrodes and supports. Of course, in some instances, it may be desired to provide the membranes 63, 64 and the grill 62 with apertures in the vicinity of the four corners thereof so that these components may be positioned over other members of the gas detection cell 60, with the screws 65 extending therethrough; in which case, the filter 61 could not be removed independently of the other components without removing the screws 65. When assembled, the laminated filter 61 is positioned beneath the aperture 25 (FIG. 1) so that it is exposed to the gaseous ambient to be monitored.

Figure 3:
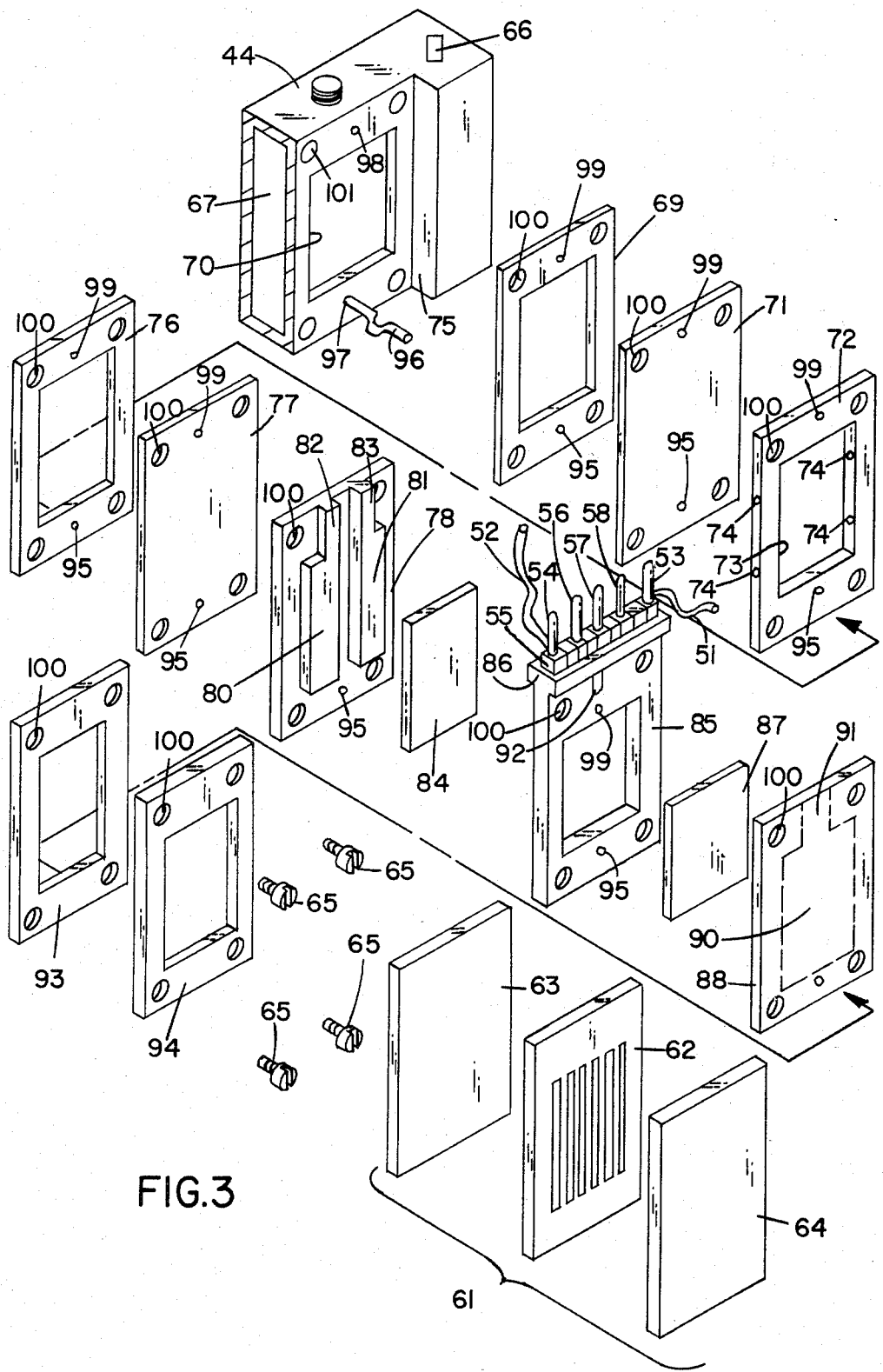
FIG. 3 is an exploded, pictorial view of an exemplary embodiment of a gas detection cell including an electrochemical gas sensor constructed in accordance with the present invention and which may be positioned within the case illustrated in FIGS. 1 and 2.

For the purpose of clarity, the electrochemical gas sensing cell as shown in an exploded view in FIG. 3 illustrates the various components of the gas sensing cell and its associated filter components out of proportion, particularly the relative thicknesses of the various components, in particular, the relative thicknesses of the membranes and filter papers.

In FIG. 3, a portion of the housing 44 is illustrated. On the flat upper surface of the housing 44, visible in FIG. 3, a small rectangular conductive plate 66 is seen. The purpose of the conductive plate 66 is to provide a conductive member which is in electrical communication with the battery 47 (FIG. 2) which is positioned in the chamber 45 (FIG. 2). It is to this flat plate 66 that the conductive lead 51 is connected so as to supply voltage of a given polarity to the pin 53. It is to be appreciated that a similar flat rectangular plate is provided to effect the electrical communication between a battery within the chamber 46 (FIG. 2) and the conductive lead 52 and thence to the pin 54.

The electrochemical gas sensing cell, as illustrated in FIG. 3, includes a reservoir 67 defined by a recess within the housing 44, a rectangular opening 70 thereinto being provided over which a gasket 69 having a large central aperture therein corresponding in size to the opening 70 is positioned. The gasket 69 may be of silicone rubber or other similar material. A rectangular sheet 71 of suitable plastics material such as microporous polytetrafluoroethylene (PTFE) is placed over the gasket 69 to close the front of the reservoir 67 and contain the electrolyte therein. A rectangular spacer 72 made of polypropylene (PPE) consisting of four interconnected legs defining an open space 73, is positioned over the sheet 71. The vertically extending side legs of a spacer 72 are each provided respectively with a pair of apertures 74 which extend therethrough and thus allow fluid communication between the space 73 defined within the spacer 72 and the gaseous ambient which is to be monitored, a slot being provided between the inwardly facing surface of a wall 75 of the housing 44 and the right-more vertically extending wall of the spacer 72. A similar slot is defined between the surface of visible vertical left-more wall of the spacer 72 and a corresponding opposed wall of that portion of the housing 44 which defines the chamber 46 (FIG. 2). Thus the space 73 is in communication with the gaseous ambient to be monitored because the case 10 (FIG. 1) is not air-tight. A rectangular gasket 76 of silicone rubber or the like and having a large center aperture therein is positioned over the spacer 74. A membrane 77 of polypropylene (PPE) is positioned over the gasket 76 and has positioned over it an electrode carrier 78. The electrode carrier 78, a thin sheet of microporous polytetrafluoroethylene (PTFE) which may be made or cut from a thin sheet. One possible material for forming the carrier 78 is sold under the trademark Gore-Tex ™ and is available from W. L. Gore and Associates, Inc. of Elkton, Md., U.S.A. The carrier 78 has thereon a pair of spaced-apart electrodes 80 and 81, which function respectively as a reference electrode and a counter electrode, the electrodes 80 and 81 are shown greatly exaggerated in thickness. The reference electrode 80 has an extension 82 thereof which extends to the upper edge of the electrode carrier 78. Similarly, the counter electrode 81 has an extension 83 thereof which extends to the upper edge of the electrode carrier 78. The reference electrode 80 is formed of platinum. The counter electrode in accordance with the present invention, is composed of carbon. In particular, the counter electrode 81 in a tested embodiment is formed by placing polytetrafluoroethylene powder (PTFE) in deionized and distilled water to provide a 23% dispersion, placing about 0.03 ml of the dispension on that portion of the carrier on which the counter electrode 81 and its associated extension is to be formed, slowly adding from about 20 to about 21 mg. of graphite to the dispersion, and then mixing and spreading the slurry over that portion of the carrier or which the counter electrode 81 and its extension 83 are to be formed. The reference electrode 80 and its associated extension 82 are formed similarly, using about 0.015 ml. of the 23% dispersion and from about 12 to about 13 mg. of Pt. The assembly is then heated to sinter the materials to the carrier 78, forming the electrodes 80 and 81, as well as the extension 82 and 83. It is to be understood that the relative ratios of the materials forming the electrodes 80 and 81 and the respective extensions 82 and 83 thereof are not critical and that the ratios can vary considerably in practical embodiments.

At least one filter 84, an inert insulator wettable by the electrolyte, such as grafted polyethylene or polypropylene membranes, treated fiber glass filter paper or filter paper is positioned over the reference electrode 80 and the counter electrode 81 for the purpose of providing a path for the electrolyte to extend upwardly in juxtaposition to the reference electrode 82 and the counter electrode 81 and to maintain the electrolyte in contact with the reference and counter electrodes regardless of the orientation of the case 10 (FIG. 1). Preferably, about three filters 84 are used, only one being illustrated for the purpose of clarity.

An electrode spacer and support 85 which may be of polypropylene (PPE) is provided and positioned over the electrode carrier 78, the electrode support 85 being provided with a central rectangular aperture therein. The electrode support 85 includes a horizontally extending portion 86 on its upper edge on which the header 55 is positioned. The pins 56 and 58 which extend through the header 55 and the portion 86 have exposed surfaces thereof, or are in contact with conductive members which could be carried by the support 85, on its obverse surface, not visible in FIG. 3, which extensions of the respective pins 56 and 58 are so positioned that they conductively contact respectively the extensions 82 and 83 of the respective reference electrode 80 and the counter electrode 81, so that electrical contact can be made to these electrodes. An additional filter 87, an inert insulator which is made of the same material as the filter 84, is positioned between the electrode support 85, which is made of polypropylene (PPE), and an electrode carrier 88. The electrode carrier 88, like the carrier 78 is made of a suitable plastics material such as microporous polytetrafluoroethylene (PTFE). The carrier 88 has positioned on its obverse surface a working or sensing electrode 90 shown in dotted lines and which is, in fact, positioned on the obverse face of the electrode carrier 88. The sensing electrode 90 includes an upward extension 91 which is positioned so as to contact a portion of the pin 57 carried by the header 55 and extending through the portion 86 of the support 85 and shown as conductive member 92. The sensing electrode 90 and its extension 91 are formed and sintered to the support 88 in the same fashion as the electrodes 80 and 81 and their extensions 82 and 83 are sintered to the support 78, using from about 29.5 to about 30.5 mg. of finely divided gold or platinum and about 0.015 ml of the 23% dispersion. The relative amounts of the materials is not critical and can vary considerably.

A rectangular, rectangularly apertured gasket 93 is positioned over the electrode carrier 88 and has, in turn, positioned over it, a metal frame member 94. Each of the sheet member 71, the spacer 72, the gasket 76, the membrane 77 and the electrode carrier 78 is provided with an aligned aperture 95 through which, when the electrochemical sensing cell is assembled, a wick 96 extends. The wick 96 extends through the apertures 95, which are aligned with an aperture 97 in the lower portion of the housing 44 so as to provide fluid communications between the electrolyte reservoir 67 and the space between the sensing electrode 90 and each of the reference electrodes 80 and the counter electrode 81. The electrolyte permeates the space between the sensing electrode 90 and the other electrodes 80 and 81 because of the position and function of the filter papers 84 and 87, even when the case 10 (FIG. 1) is orientationed other than upright.

A further aperture 98, provided in the upper portion of the housing 44, is aligned with corresponding apertures 99 in the upper central portions of the gasket 69, the sheet 71, the spacer 72, the gasket 76, the membrane 77, the electrode carrier 78 and the support 85 so that gas produced between the electrodes will be able to flow back to the reservoir 67. The aperture in the upper portion of electrode carrier 78 is not visible in FIG. 4, but is present between the extensions 82 and 83. The sheet 71, the spacer 72, the gasket 76, the membrane 77, the electrode carrier 78, the electrode spacer 85, the electrode carrier 88, the gasket 93 and the frame 94 are provided in the vicinity of their respective corners with respective apertures 100 which are in alignment with four respective threaded bores 101 in the housing 44. This allows the aforementioned rectangular members to be closely positioned adjacent one another so that the four screws 65 can hold the electrochemical sensing cell members in stacked relationship over the reservoir 67.

A filter 61, also visible in FIG. 2, is positioned over the frame 94. The filter 61 is composed of a laminate consisting of a membrane 63 of dimethyl silicone, an apertured rigid support 62 (preferably a grill) which is composed of a chemically inert substantially rigid material, such as the material sold under the trademark Tefzel ® as noted above and a further membrane 63 which is composed of propylene (PPE), such as a 1 mm. thick membrane of this material. The membrane 63 could also be a membrane of polypropylene (PPE), in which case firebrick coated with a permsel material would be placed within the apertures in the rigid support 62. The firebrick is inert and serves as a support for the permsel material, such as ethanolamine, which can remove interferents, but not $H_2S$.

The membrane 63 is fixed to one side of the grill 62 by a suitable adhesive applied about its edges. The membrane 64 is fixed to the other side of the grill by a suitable adhesive applied about its edges. The filter 62 is then held upright in a vacuum oven under vacuum at from about 50° C. to about 60° for a number of hours, such as overnight. A hardener is then applied to the edges of the polypropylene (PPE) membrane 64 and it is allowed to dry for at least four hours. The members 62-64 are laminated so as a practical matter consist of a single unit, the filter 61. When the apparatus is assembled for operation, the filter 61 is positioned over the frame 94 before the cell is slidably pushed into the upper member 11, (FIG. 2) of the case 10 so that the filter 61, with the membrane 64 outermost, is positioned beneath the aperture 25 (FIG. 1). In the case where the membrane 63 is made of polypropylene (PPE), the laminate also involves the placing of the coated firebrick within the aperture of grill 62 before placing the membrane 64 thereon and the application of a hardner to edges both of the membranes 63 and 64.

In FIG. 4, a portion of the housing 44, shown pictorially in FIG. 2, is illustrated diagrammatically by a dashed line and shown to include associated therewith the reference electrode 80, the counter electrode 81 and the sensing electrode 90 with their associated pins 56-58, illustrated diagrammatically as well. In addition, the battery 47 and the battery 48, as well as the third battery 102, which is not visible in FIG. 2, with their associated pins 53 and 54 are also diagrammatically illustrated. The buzzer 31 visible in FIG. 1, is shown diagrammatically in FIG. 4. As mentioned above, the circuit components of the present invention may be potted and positioned within the case 10 (FIG. 1). The potted circuit components include accessible conductive bayonet connectors, illustrated in FIG. 4 as connectors 103-107, which are so positioned within the case 10 (FIG. 1) that the conductive pins 56-58, 54 and 53 can be respectively inserted thereinto to provide electrical communcation when the housing 44 (FIG. 2) is slidably inserted into the case 10. The bayonet connector 107 establishes a reference ground connection between the circuitry of FIG. 1 and the power pack, consisting of the series connection of the batteries 47, 48 and 102, the bayonet connector 106 providing for a positive power connection to the various circuit components from the power pack. The circuit includes a three terminal adjustable current source 108 which has its positive terminal connected to the positive voltage point defined by the connector 106, its negative terminal being connected to reference ground via a series connection consisting of a diode 110, a fixed resistor 111, a fixed resistor 112, and a fixed resistor 113. The respective ends of the resistors 112 are connected to terminals A and B, respectively, allowing these points to be connected to circuit terminals C and D by jumpers so that the size of the resistor 112 can be selected and connections made from either of the points A and B to either of the points C and D to provide for detection of different agents. In either case the size of the resistor 112 can be selected in accordance with the agent sought to be detected. Indeed, in some cases, the resistor 112 can be made zero. As illustrated, the terminal A is connected to the terminal D and the terminal B is connected to the terminal C, these being used for the detection $H_2S$. The negative terminal of the adjustable current source 108 is connected to its third terminal via a variable resistor 114 which is a bias adjusting resistor. The third terminal of the variable current source 108 is also connected to reference ground via a fixed resistor 115 connected in series with a potentiometer 116. The potentiometer 116 is utilized for zero adjustment. The junction between the resistor 115 and the potentiometer 116 is connected conductively to a junction between the cathode of the diode 110 and one end of the fixed resistor 111.

The circuitry includes a first operational amplifier 117 having its inverting input connected to the reference electrode 80, via the bayonet connector 103 and the pin 56. The noninverting input of the operational amplifier 117 is connected to the junction between the fixed resistor 112 and the fixed resistor 113 via the terminal C and the terminal B. The output terminal of the operational amplifier 117 is connected to the counter electrode 81 via the bayonet connector 104 and the pin 58. A capacitor 118 is connected between the output terminal of the amplifier 117 and its inverting input terminal.

A second operational amplifier 120 has its inverting input terminal connected to the sensing electrode 90, via a resistor 121, the bayonet connector 105 and the pin 57. The noninverting input terminal of the operational amplifier 120 is connected conductively to the intersection between the resistor 111 and the resistor 112 via the terminals A and D. The output terminal of the second operational amplifier 120 is coupled to its inverting input terminal via a capacitor 122 which is connected in parallel with a resistor 123 and in parallel with a temperature-sensitive temperature compensating resistor 124.

A third operational amplifier 125, having its output terminal directly connected to its inverting input terminal is provided, its noninverting input terminal being directly connected to the noninverting input terminal of the second operational amplifier 120, the operational amplifiers 120 and 125 thus operate at the same voltage level. The output terminal of the third operational amplifier 125 is connected to reference ground via a fixed resistor 126 and, via a fixed resistor 127 to the inverting input terminal of a fourth operational amplifier 128, which has its noninverting input terminal conductively connected to the output terminal of the second operational amplifier 120. A variable resistor 130, which provides for span adjustment, is connected between the output terminal of the operational amplifier 128 and its inverting input terminal.

A fifth operational amplifier 131 has its noninverting input terminal connected to the output terminal of the fourth operational amplifier 128 via a fixed resistor 132. The noninverting input terminal of the operational amplifier 131 is connected to ground reference potential via a fixed resistor 133. The output terminal of the operational amplifier 131 is connected to its inverting input terminal via a fixed resistor 134, its inverting input terminal being connected, via a fixed resistor 135 to the wiper of the potentiometer 116. The output terminal of the operational amplifier 131 is connected to a bar display driver 136 which has a power input terminal connected to the point of positive voltage, via a switch 137, which switch 137 may be turned on by a user by depressing the button 37 (FIG. 1) whenever the user wishes to obtain a quantitative reading of the gaseous agent, $H_2S$ in the specific example, sought to be detected in the atmosphere or other gaseous ambient being monitored. One input power connection to the driver 136 is provided to ground via a fixed resistor 139, a fixed resistor 138 being connected in series with the resistor 139 and two other power connections to the driver 136.

The output terminal of the operational amplifier 131 is also connected to the noninverting input terminal of a further operational amplifier 140, via a fixed resistor 141, this noninverting input terminal also being connected to the point of reference ground potential via a fixed resistor 142. The inverting input terminal of the operational amplifier 140 is connected to the wiper of a potentiometer 143, via a fixed resistor 144. The potentiometer 143 is connected between the point of reference ground potential and the electrical point between the potentiometer 116 and the fixed resistor 115. A diode 145 is connected between the switch 137 and the inverting input terminal of the operational amplifier 140, the cathode of the diode 145 being connected to the inverting input terminal. The output of the operational amplifier 140 is connected to the base of an NPN transistor 146 via a fixed resistor 147. The emitter of the transistor 146 is connected to the point of ground reference potential, its collector being connected to the point of positive potential, via the buzzer 31.

The point of positive voltage is also connected to the inverting input terminal of an additional operational amplifier 148, via the series connection provided by the switch 137, a diode 150 and a fixed resistor 151. The noninverting input terminal of the operational amplifier 148 is connected to the point of ground reference potential via a fixed resistor 152 and via a further fixed resistor 153 to an output terminal of a ripple carry binary counter 154, which has three of its other terminals connected respectively via a capacitor 155, a fixed resistor 156 and a fixed resistor 157 to a common circuit point. A further operational amplifier 158 has its noninverting input terminal connected to an output from the counter 154, its inverting input terminal being directly conductively connected to its output terminal, which is also connected conductively to the backplate of a liquid crystal bar graph display member 160. The counter 154 is operatively arranged to function as an oscillator having a pulse output which, via the respective operational amplifiers 148 and 158 provides for flashing the LED 166 ON and OFF and energizes the liquid crystal bar graph display 160. The liquid crystal bar graph display 160 is provided with 10 inputs, via respective capacitors 167, from the driver 136, each one being associated with a particular and increasing level of detection, for example, from zero to 50 parts per million of the gaseous agent, given as $H_2S$ as the specific example, sought to be detected.

A eleventh input signal to the liquid crystal display 160 is provided from a PNP transistor 161, the collector of which is coupled to the ninth input of the liquid crystal display 160 via a capacitor 162. The emitter of the transistor 161 is directly connected to the point of ground reference potential, its base being connected to the output terminal of the operational amplifier 148 via a fixed resistor 163. The output terminal of the operational amplifier 148 is connected to its inverting input terminal via a fixed resistor 164, and via a further fixed resistor 165 to the anode of a light emitting diode 166, which has its cathode connected to the collector of the transistor 146. The light emitting diode flashes ON and OFF whenever it is provided with an input from the operational amplifier 148 and the transistor 146 is turned ON, this transistor being turned ON at a threshold level of concentration of the agent to be detected, determined by the setting of the potentiometer 143. The buzzer 31 also is turned ON by conduction of the transistor 146.

The eleventh input signal to the liquid crystal display 160 provides for monitoring the condition of the batteries 47, 48 and 102. The ninth bar on the display 160 becomes visible whenever the display 160 has not been called upon, by the depression of the button 37 and the closing of the switch 137, to indicate level of the agent sought to be detected, and does indicate that the battery power pack has a sufficiently high voltage level. When the switch 137 is closed, the ninth bar on the display 160 is no longer turned ON by the signal indicative of power pack voltage level; rather, the first to tenth bars become visible one after another as the concentration of the $H_2S$ increases from zero to 50 ppm.

The bias adjustment provided by the variable resistor 114 and the threshold adjustment provided by the potentiometer 143 are set during initial testing and assembling, once the particular gas to be detected has been selected. The zero adjustment provided by the potentiometer 116 and the span adjustment provided by the variable resistor 130 are made periodically, for example, once a week using a standard gas concentration.

In a practical working embodiment of the circuit shown in FIG. 4, used to measure $H_2S$ concentration, the circuit components used were as stated below:

| | | |
|---|---|---|
| Variable resistor 114 | 1K ohms | Capacitor 118 .1 μf. |
| Variable resistor 130 | 100K ohms | Capacitor 122 .1 μf. |
| Resistor 111 | 2.4K ohms | Capacitor 155 470 μf. |
| Resistor 112 | 1.5K ohms | Potentiometer 116 100K ohms |
| Resistor 113 | 3.6K ohms | Potentiometer 143 100K ohms. |
| Resistor 115 | 6.8K ohms | |
| Resistor 121 | 150K ohms | |
| Resistor 123 | 41K ohms | |
| Resistor 124 | 1K ohms at 25° C. | |
| Resistor 126 | 24K ohms | |
| Resistor 127 | 24K ohms | |
| Resistor 132 | 100K ohms | |
| Resistor 133 | 100K ohms | |
| Resistor 134 | 1 M ohms | |
| Resistor 135 | 1 M ohms | |
| Resistor 137 | 3.3K ohms | |
| Resistor 138 | 5.6K ohms | |
| Resistor 141 | 100K ohms | |
| Resistor 142 | 100K ohms | |
| Resistor 144 | 1 M ohms | |
| Resistor 147 | 2.2K ohms | |
| Resistor 151 | 5.6 M ohms | |
| Resistor 152 | 68K ohms | |
| Resistor 153 | 24K ohms | |
| Resistor 156 | 1.2 M ohms | |
| Resistor 157 | 5.6 M ohms | |
| Resistor 163 | 47K ohms | |
| Resistor 164 | 22 M ohms | |
| Resistor 165 | 200 ohms. | |

The operational amplifiers 117, 120, 128 and 125 in a practical embodiment are realized from respective quarters of an ICL 7642BCPD available from Intersil. The operational amplifiers 131, 140, 148 and 158 in the embodiment are realized from respective quarters of an ICL 7642BCPD available from Intersil. The counter 154 in the practical embodiment is a CD 4060 available from National Semiconductor. The adjustable current source 108 is a three-terminal source LM 134 available from National Semiconductor. The pin numbers for the above-mentioned integrated circuits are set out in FIG. 4.

The bar display driver 136 is available under the designation LM3914 from National Semiconductor. The liquid crystal bar display 160 is a conventional display having provisions for ten signal inputs, one of these being used to monitor the battery voltage when the display is not being used to monitor concentration of the agent to be detected.

The electrochemical gas sensor constructed in accordance with the present invention, achieves two distinct improvements over prior art sensors which use gold or platinum counter electrodes. The configuration of the electrochemical gas sensing cell and the electrolyte according to the present invention, makes it possible to operate the sensing electrode at a reduced potential. By utilizing the carbon counter electrode, two distinctive advantages can be achieved; that is, reduced cost and poison resistance. Gold or platinum powder, used in conventional sensors, is more than 1,000 times more expensive than the carbon used in the sensor made in accordance with the present invention. Since the cost of the noble metal used in an electrode is a significant portion of the cost of the sensor, the replacement of a noble metal with carbon constitutes a significant saving. It is well known to those skilled in the art that platinum or gold electrodes can be easily poisoned by compounds normally found in some test environments. The carbon counter electrode utilized in the present invention is resistant to most of the compounds which inactivate noble metal electrodes.

By allowing the sensing electrode bias in the detection cell of the present invention to be operated below 300 mv., in a specific example at about 250 mv., with respect to the platinum air reference electrode, the electrochemical cell according to the present invention eliminates responses of the sensor to any interfering gas oxidized in voltage ranges above 300 mv. and in the specific example at the 250 mv. level, thereby increasing the specificity of the sensor.

As pointed out above, the resistor 112 is desirably connected to the operational amplifier inputs via terminals A–D so that the circuit of FIG. 4 can be readily modified to detect various other gaseous agents. In some cases, the capacitor 122 and the temperature-compensating resistor 124 may also be changed to modify the circuit for other gaseous agents. The values for the resistors 122 and 124 and the capacitor 112 are used when the agent is $H_2S$.

The electrolyte may be a nonaqueous electrolyte which consists of either (1) propylene carbonate or (2) n-methyl-2-pyrrolidone and one of the conductive compatible salts as a supporting electrolyte, one such compatible salt being tetrabutyl ammonium tetrafluoroborate (TBA . $BF_4$). The electrolyte using the second (2) material as the solvent is a preferred and novel electrolyte, especially useful in $H_2S$ sensors.

The foregoing text and accompanying drawings relate to exemplary embodiments of the present invention and have been set out, not by way of limitation, but by way of illustration. Numerous other embodiments and variants are possible without departing from the spirit and scope of the invention, the scope of the invention being defined by the appended claims.

What is claimed is:

1. An electrochemical gas sensor comprising a sensing electrode, a reference electrode and a counter electrode, said counter electrode being made of carbon, said sensing electrode, reference electrode and counter electrode are spaced apart, and
a nonaqueous electrolyte in contact with said electrodes and in the space between said sensing electrode and each of said counter electrode and said reference electrode, said electrolyte including n-methyl-2-pyrrolidone and at least one conductive salt.

2. The electrochemical gas sensor according to claim 1, wherein said reference electrode and said sensing electrode are each of platinum.

3. The electrochemical gas sensor according to claim 1, including an electrode carrier, said counter electrode being composed of a composite formed of graphite and polytetrafluoroethylene on said carrier.

4. The electrochemical gas sensor of claim 1 wherein said conductive salt includes tetrabutyl ammonium tetrafluoroborate.

5. An electrochemical gas detection cell comprising: a gas sensor having a sensing electrode, a reference electrode and a counter electrode spaced apart from each other, said counter electrode being made of carbon; means for supplying an electrolyte to the space between said sensing electrode and each of said counter electrode and said reference electrode; and filter means positioned between said sensing electrode and a gaseous ambient for reducing response to interferents, said electrolyte being nonaqueous and including n-methyl-2-pyrrolidone and at least one conductive salt.

6. The electrochemical gas detection cell according to claim 5, wherein said reference electrode and said sensing electrode are each of platinum.

7. The electrochemical gas detection cell according to claim 5, including an electrode carrier, said counter electrode being composed of a composite formed of graphite and polytetrafluoroethylene on said carrier.

8. The electrochemical gas detection cell according to claim 5, wherein said conductive salt includes tetrabutyl ammonium tetrafluoroborate.

9. A system for detecting gas, including a gas sensing cell including a sensing electrode, a reference electrode and a counter electrode spaced apart from each other, said counter electrode being made of carbon; means for supplying an electrolyte to the space between said sensing electrode and each of said reference electrode and said counter electrode; circuit means for maintaining the voltage of said sensing electrode with respect to said reference electrode in a range below 300 mv.; and means responsive to an output from said cell to provide at least one indication of concentration of a gas in an ambient to be monitored, said electrolyte being nonaqueous and including n-methyl-2-pyrrolidone and at least one conductive salt.

10. A system according to claim 9, wherein said circuit means includes means for maintaining the voltage of said sensing electrode with respect to said reference electrode at about 250 mv.

11. The system according to claim 9 wherein said conductive salt includes tetrabutyl ammonium tetrafluoroborate.

12. An electrochemical gas sensor comprising a sensing electrode, a reference electrode and a counter electrode, said sensing electrode, reference electrode and counter electrode are spaced apart, and
a nonaqueous electrolyte in contact with said electrodes and in the space between said sensing electrode and each of said counter electrode and said reference electrode, said electrolyte including n-methyl-2-pyrrolidone and at least one conductive salt.

13. The electrochemical gas sensor of claim 12 wherein said conductive salt includes tetrabutyl ammonium tetrafluoroborate.

14. An electrochemical gas detection cell comprising:

a gas sensor having a sensing electrode, a reference electrode and a counter electrode spaced apart from each other; and means for supplying a nonaqueous electrolyte to the space between said sensing electrode and each of said counter electrode and said reference electrode; said electrolyte including n-methyl-2-pyrrolidone and at least one conductive salt.

15. The electrochemical gas detection cell according to claim 14, wherein said conductive salt includes tetrabutyl ammonium tetrafluoroborate.

* * * * *